United States Patent [19]

Moniot et al.

[11] 4,326,076
[45] Apr. 20, 1982

[54] METHOD FOR PREPARING THE OPTICALLY ACTIVE ISOMER OF 2,2-[[5-[3-[(1,1-DIMETHYLETHYL)AMINO]-2-HYDROXYPROPOXY]-1,2,3,4-TETRAHYDRO-2,3-NAPHTHALENE-DIYL]BIS(OXY)]-BIS[N,N-DIPROPYLACETAMIDE]

[75] Inventors: Jerome L. Moniot, Richboro, Pa.; Rita T. Fox, Princeton; Francis A. Sowinski, Edison, both of N.J.

[73] Assignee: E. R. Squibb & Sons, Inc., Princeton, N.J.

[21] Appl. No.: 195,684

[22] Filed: Oct. 9, 1980

[51] Int. Cl.³ .................. C07C 103/24; C07C 103/28
[52] U.S. Cl. .................................... 564/156; 564/157
[58] Field of Search ............................... 564/157, 156

[56] References Cited

U.S. PATENT DOCUMENTS 3,935,267 1/1976 Hauck et al. ................. 260/326.5 L
4,165,384 8/1979 Carlsson et al. ..................... 564/156

OTHER PUBLICATIONS

Nelson et al., *J. Org. Chem.*, vol. 42, No. 6, 1977, pp. 1006–1012.

Baldwin et al., *J. Org. Chem.*, 43, (25 4876 (1978)).
Condon et al., *J. Med. Chem.*, vol. 21, 1978, p. 913.
Borowitz et al., *Organic Preparations and Procedures Int.*, 9(6), 1977. PP. 257–262
Weiss, Synthetic Ionophores, Belfer Graduate Schoole of Science, Yeshiva University, 1976.

*Primary Examiner*—Charles F. Warren
*Attorney, Agent, or Firm*—Lawrence S. Levinson; Burton Rodney

[57] ABSTRACT

A method is provided for preparing the optically active isomer [2R-[2α,3α,5(R*)]]-2,2'-[[5-[3-[(1,1-dimethylethyl)amino]-2-hydroxypropoxy]-1,2,3,4-tetrahydro-2,3-naphthalenediyl]bis(oxy)]bis-[N,N-dipropylacetamide] having the structure

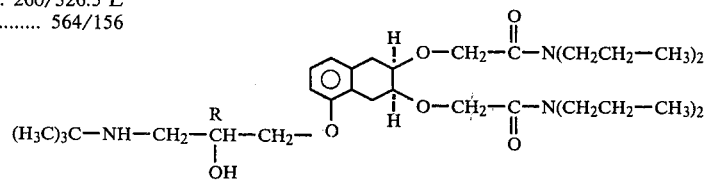

which is useful as an antiarrhythmic agent.

7 Claims, No Drawings

METHOD FOR PREPARING THE OPTICALLY ACTIVE ISOMER OF 2,2'-[[5-[3-[(1,1-DIMETHYLETHYL)AMINO]-2-HYDROXYPROPOXY]-1,2,3,4-TETRAHYDRO-2,3-NAPHTHALENE-DIYL]BIS(OXY)]BIS[N,N-DIPROPYLACETAMIDE]

FIELD OF THE INVENTION

The present invention relates to a method for preparing the optically active isomer [2R-[2α,3α,5(R*)]]-2,2'-[[5-[3-[(1,1-dimethylethyl)amino]-2-hydroxypropoxy]-1,2,3,4-tetrahydro-2,3-naphthalenediyl]bis(oxy)]-bis[N,N-dipropylacetamide], which is useful in treating arrhythmia.

BACKGROUND OF THE INVENTION

U.S. patent application Ser. No. 195,685, filed Oct. 9, 1980, by Hauck et al, now pending discloses and claims anti-arrhythmic compounds having the structure

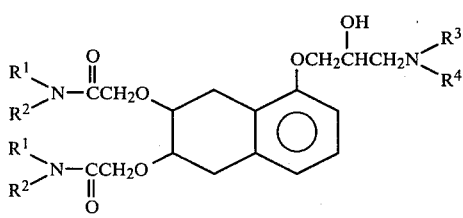

wherein $R^1$ and $R^2$ may be the same or different and can be hydrogen, lower alkyl, lower alkenyl or hydroxy-lower alkyl, or $R^1$ and $R^2$ may be taken together with the nitrogen atom to which they are attached to form a heterocyclic radical which may contain in addition to such nitrogen atom, one other heteroatom which can be nitrogen, oxygen or sulfur; and $R^3$ and $R^4$ may be the same or diffferent and can be hydrogen or lower alkyl, and acid-addition salts and stereoisomers thereof. The specific compound 2,2'-[[5-[3-[(1,1-dimethylethyl)amino]-2-hydroxypropoxy]-1,2,3,4-tetrahydro-2,3-naphthalenediyl]bis(oxy)]bis[N,N-dipropylacetamide] and its cis and trans isomers are disclosed and claimed.

The latter compound in cis form may be resolved into four possible optical isomers, namely, A.
[2S-[2α,3α,5(S*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

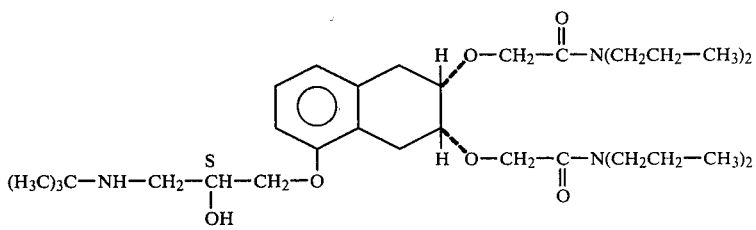

B.
[2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

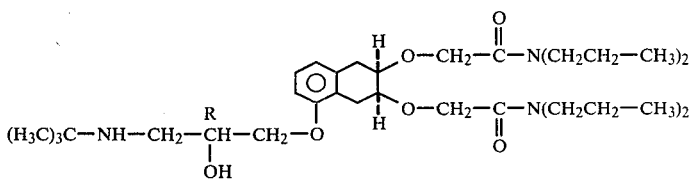

C.
[2R-[2α,3α,5(S*)]]-2,2'-[[5,[3-[(1,1-Dimethylethyl)amino]-2-hydroxypropoxy]-1,2,3,4-tetrahydro-2,3-naphthalenediyl]bis(oxy)]bis[N,N-dipropylacetamide]

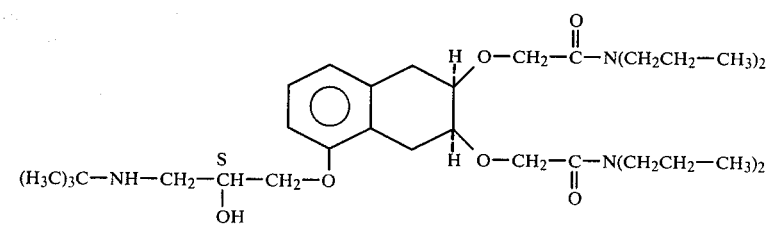

D.
[2S-[2α,3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

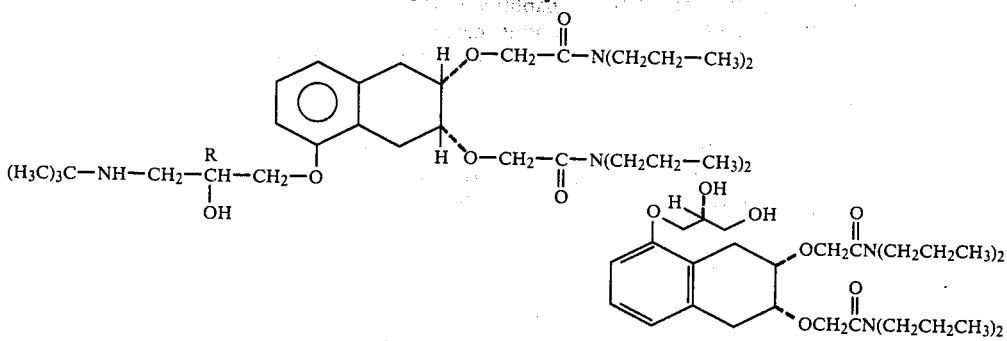

DESCRIPTION OF THE INVENTION

The present invention relates to a method for preparing the isomer of structure

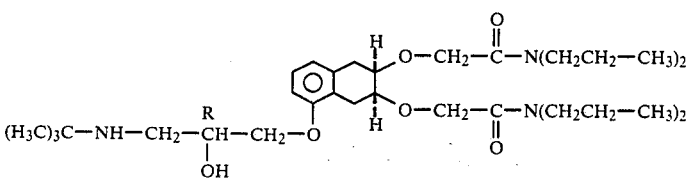

which method may be represented diagrammatically as follows:

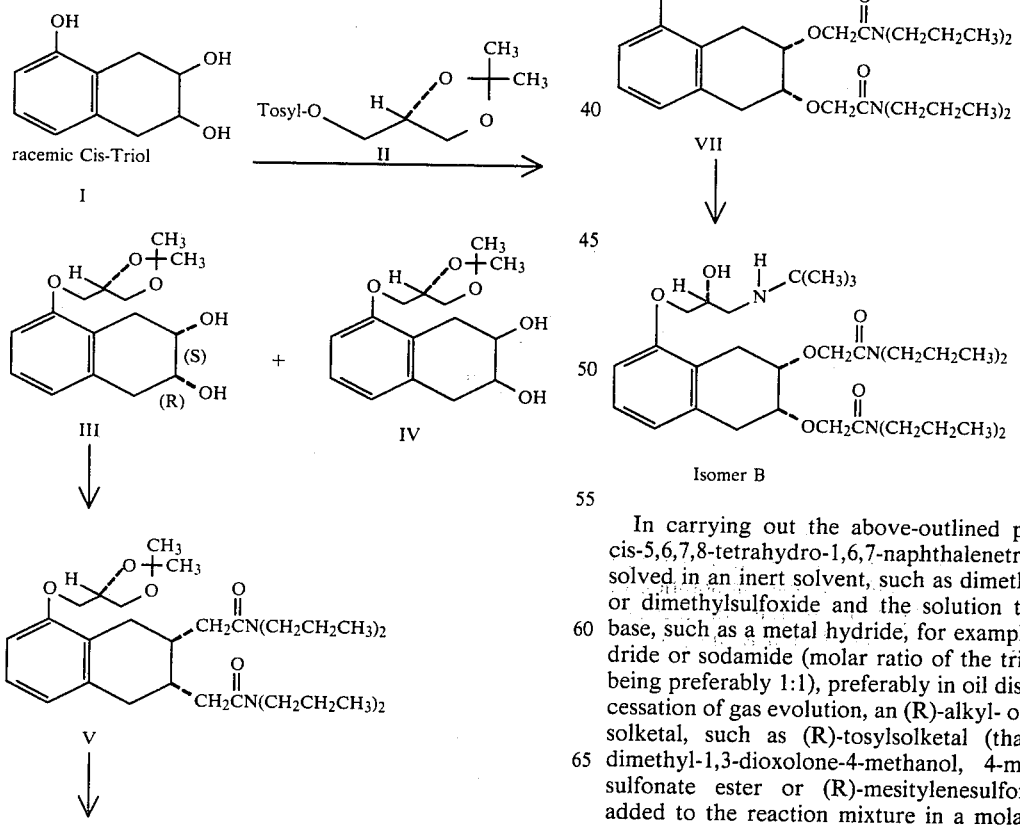

In carrying out the above-outlined procedure, the cis-5,6,7,8-tetrahydro-1,6,7-naphthalenetriol is dissolved in an inert solvent, such as dimethylformamide, or dimethylsulfoxide and the solution treated with a base, such as a metal hydride, for example, sodium hydride or sodamide (molar ratio of the triol to the base being preferably 1:1), preferably in oil dispersion. After cessation of gas evolution, an (R)-alkyl- or aryl-sulfonyl solketal, such as (R)-tosylsolketal (that is, (R)-2,2-dimethyl-1,3-dioxolone-4-methanol, 4-methylbenzene-sulfonate ester or (R)-mesitylenesulfonylsolketal is added to the reaction mixture in a molar ratio to the naphthalenetriol of from about 1:1 to about 1.5:1, the reaction mixture is stirred under inert atmosphere and heated to and maintained at a temperature of from about 30° to about 80° C. for a period of from about 1 to about 24 hours. Next, the reaction mixture is cooled, concentrated and recrystallized to form a mixture of the acetonide intermediates of formulae III (1-isomer) and IV (d-isomer) wherein the two alcoholic hydroxyl groups of each remain free while the phenolic hydroxyl group is converted to the ether.

The 1-isomer (compound III) is separated from the mixture by ether trituration and recrystallization, and dissolved in dimethylsulfoxide or dimethylformamide, together with an N,N-dipropylhaloacetamide, such as N,N-dipropylchloro, iodo or bromoacetamide (employing a molar ratio of acetamide to III of from about 2:1 to about 3:1). A base, such as metal hydride, for example, sodium hydride (in oil dispersion) or sodamide is added to the solution and the resulting suspension is stirred for a period of from about 1 to about 48 hours under inert atmosphere (preferably argon) at room temperature to form the formula V compound. The formula V compound is extracted from the reaction mixture, dried and then slurried in water for use in hydrolyzing the acetonide ring and making the compound of formula VI.

To the aqueous slurry of the compound of formula V is added a lower alkanol solvent, such as methanol, ethanol or a mixture thereof, and an inert solvent, such as acetone or tetrahydrofuran and a mineral acid, such as hydrochloric acid. The mixture is heated to a temperature within the range of from about 25° to about 95° C. for up to 120 minutes or more, cooled and concentrated to a dense oil which may be further purified.

The so-formed compound of formula VI is dissolved in a basic solvent, such as pyridine and/or a chlorinated hydrocarbon solvent, such as chloroform and is maintained at a temperature of from about −100° C. to about −10° C. under an inert atmosphere, preferably argon. Mesitylenesulfonyl chloride is added employing a molar ratio of same to the compound VI of from about 1:1 to about 1.5:1 and the reaction mixture maintained below 0° for a period of up to 24 hours or more. Thereafter, the compound VII present in the reaction mixture is removed therefrom by solvent extraction and is employed in making the isomer B as described below.

A solution of compound VII in t-butylamine as the solvent, in a sealed reaction vessel, (employing a molar ratio of VII to amine of from about 1:1 to about 20:1 or more, is heated at a temperature of up to 90° C., for up to 48 hours or more. The resulting solution is treated with an inert hydrocarbon solvent, such as hexane, heptane or benzene, and the solution is filtered and concentrated. A dense oil is formed from which isomer B is partitioned and extracted.

The isomer of formula B has anti-arrhythmic activity as indicated by the Harris coronary-ligated dog test described by Harris, A. S., Circulation 1:1318–1328, 1950 which activity is substantially superior to that found in Isomers A, C and D described hereinbefore. Thus, the isomer B is useful in the treatment of arrhythmia in mammalian species, for example, rats and dogs.

Isomer B as well as its physiologically acceptable acid salts may be compounded according to pharmaceutical practice in oral or parenteral dosage forms, such as tablet, capsules, elixirs, injectables or powders for administration of about 10 mg to 2 gr per day, preferably 125 mg to 175 mg per day, in 2 to 4 divided doses.

The following Example represents a preferred embodiment of the present invention. All temperatures are in degrees Centigrade.

EXAMPLE

[2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

A.

[2R-[2α,3α,5(R*)]]-5-[(2,2-Dimethyl-1,3-dioxolan-4-yl)methoxy]-1,2,3,4-tetrahydro-2,3-naphthalenediol (III) and
[2S-[2α,3α,5(R*)]]-5-[(2,2-Dimethyl-1,3-dioxolan-4-yl)methoxy]-1,2,3,4-tetrahydro-2,3-naphthalenediol (IV)

To a solution of cis-5,6,7,8-tetrahydro1,6,7-naphthalenetriol (21.6 g, 0.12 mol) in dimethylformamide (200 ml) at 23° is added 6.04 g sodium hydride 50% oil dispersion (after prior washing with hexane 50 ml) and 15 minutes after cessation of gas evolution, (R)-tosylsolketal II (that is, (R)-2,2-dimethyl-1,3-dioxolane-4methanol, 4-methylbenzenesulfonate ester prepared as described by J. J. Baldwin, et al., *J. Org. Chem.*, 43, (25 4876 (1978)) (34.2 g, 0.12 mol) is added all at once and rinsed in with dimethylformamide (50 ml). The reaction mixture is stirred under argon and heated to and maintained at 65° C. for 26 hours.

The mixture is cooled to 23°, diluted with methanol (20 ml) and concentrated at 55° C., 1 mm Hg, to a dark brown semi-solid. The residue is taken up in chloroform (0.7 l), extracted with brine (0.3 l), water (1 l.) and saturated NaHCO$_3$ solution. Each of the aqueous layers is reextracted with CHCl$_3$ (1 l.) and the combined organic layers are dried over K$_2$CO$_3$, filtered and evaporated to give a dark tan semi-solid residue. The residue is then triturated with ether (1 l.) and the resulting crystals removed by filtration. They are washed with several 50 ml portions of ether until the color remains unchanged and then with 50 ml of cold methanol. This treatment gives nearly colorless product largely free of the second diastereomer. Recrystallization from 450 ml of hot chloroform then affords 31.9 g (46%) of pure product, m.p. 149°–150°, [a]$D^{22}$= −2.08°(c=1.70, methanol).

B.

[2R-[2α,3α,5(R*)]]-2,2'-[[5-[(2,2-Dimethyl-1,3-dioxolan-4-yl)methoxy]-1,2,3,4-tetrahydro-2,3-naphthalenediyl]-bis(oxy)]bis[N,N-dipropylacetamide](V)

To a solution of [2R-[2α,3α,5(R*)]]-5-[(2,2-dimethyl-1,3-dioxolan-4-yl)methoxy]-1,2,3,4-tetrahydro-2,3-naphthalenediol III (8.23 g, 0.028 mol) and chloroacetamide (10.3 g, 0.058 mol) in dry dimethylsulfoxide (150 ml) is added 50% oil dispersion of sodium hydride (2.78 g, 0.058 mol) after washing with hexane, and the suspension is allowed to stir at 22° for 18 hours under argon at room temperature. To the resulting deep tan solution is added methanol (10 ml) and the solution is poured into water (800 ml) and extracted with ether (2×600 ml). The organic layer is reextracted with brine (300 ml) and dried over potassium carbonate, filtered and evaporated to a tan crystalline mass (16.2 g). The material is dissolved in a minimum volume of boiling isopropyl ether and allowed to stand to give after hexane washing, air drying and vacuum drying (2 mm, 60°, 2 hours) 13.35 g of the title compound (V) as colorless rosettes of needles, m.p. 77°–78°, a$_D$= +1.0° (c=2, MeOH). R$_f$=0.35, SiO$_2$, 0.5% MeOH/CHCl$_3$.

C.
[2R-[2α,3α,5(R*)]]-2,2'-[[5-(2,3-Dihydroxypropoxy)-1,2,3,4-tetrahydro-2,3-naphthalenediyl]bis(oxy)-bis[N,N-dipropylacetamide](VI)

To a slurry of [2R-[2α,3α,5(R*)]]-2,2'-[[5-[(2,2-dimethyl-1,3-dioxolan-4-yl)methoxy]1,2,3,4-tetrahydro-2,3-naphthalenediyl]bis(oxy)]bis[N,N-dipropylacetamide] V (12.5 g, 0.022 mol) in water (30 ml) is added acetone (20 ml) and absolute ethanol (50 ml) and 5% aqueous hydrochloric acid (70 ml) and the mixture is heated on a steam bath for 30 minutes with aliquots of absolute ethanol added as required to maintain a clear solution. The mixture is cooled to room temperature, diluted with benzene (500 ml) and concentrated to a dense oil. The resulting oil is partitioned between brine and chloroform and the organic layer is dried over $K_2CO_3$, filtered and evaporated to yield a dense oil. Drying at 0.5 mm Hg vacuum at 45° C. for 2 hours affords the title compound as a dense oil, 11.9 g (some $CHCl_3$ remains) $\alpha_D = -8.1°$ (c=4, MeOH). $R_f = 0.15$, $SiO_2$, 0.5% MeOH/$CHCl_3$. Yield 95%.

D.
[2R-[2α,3α,5(R*)]]-2,2'-[[1,2,3,4-Tetrahydro-5-[2-hydroxy-3-[[(2,4,6-trimethylphenyl)sulfonyl]oxy]-propoxy]-2,3-naphthalenediyl]bis(oxy)]bis[N,N-dipropylacetamide] (VII)

To a stirred solution of [2R-[2α,3α,5(R*)]]-2,2'-[[5-(2,3-dihydroxypropoxy)-1,2,3,4-tetrahydro-2,3-naphthalenediyl]bis(oxy)]bis[N,N-dipropylacetamide] VI (11 g, 0.0205 mol) in pyridine (50 ml) and chloroform (70 ml) at −30° C. under argon is added mesitylenesulfonyl chloride (4.5 g, 0.0206 mol) as a finely ground powder, portionwise over 15 minutes and the resulting light yellow solution is stored in a freezer (−15° C.) overnight. The clear yellow solution is poured onto a mixture of ice and saturated solution of ammonium sulfate and is extracted with ether (2×500 ml). The ether layer is repeatedly extracted with saturated aqueous solution of cupric sulfate until there is no further color changes. The organic layer is dried over $Na_2SO_4$, filtered and concentrated to give 13.2 g of light yellow oil. The oil is dried at 0.5 mm Hg/50° for 1 hour to yield a dense oil 12.2 g. TLC reveals trace impurities of unreacted starting material, tlc purity of major product ≧93% of the title compound VII, $\alpha_D = +0.4°$ (c=4, MeOH). The product is used without further purification. Yield 83% $R_f = 0.4$, $SiO_2$, 0.5% MeOH/$CHCl_3$.

E.
[2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]-bis(oxy)]bis[N,N-dipropylacetamide] (Isomer B)

A stirred solution of 48.7 g (0.068 mole) of [2R-2α,3α,5(R*)]]-2,2'-[[1,2,3,4-tetrahydro-5-[2-hydroxy-3-[[(2,4,6-trimethylphenyl)sulfonyl]-oxy]propoxy]-2,3-naphthalenediyl]bis(oxy)]bis-[N,N-dipropylacetamide] VII in 150 ml of tert-butylamine is stirred in a 1 l. pressure vessel for 18 hours. The light orange solution is treated with hexane (50 ml) and after standing 20 minutes the solution is filtered and concentrated to dryness. The dense oil is taken up in ether and partitioned with brine and then 5% aqueous hydrochloric acid. The acidic layer is made alkaline to pH=9 with aqueous KOH (25%) with ice cooling and partitioned with ether (2×600 ml), the ether layer dried over $MgSO_4$, filtered and evaporated to a dense oil which, after vacuum (0.5 mm) drying at 70° for 20 minutes, gives 34.2 g of a glassy viscous oil. This material is chromatographed on 700 g of alumina (act III) in a 70 mm column. A 96:4 ether/methanol mixture removes the two impurities of $R_f$ 0.74 and 0.63 ($Al_2O_3$—10% methanol in ether) and 10% methanol in ether removes the pure product. After rechromatographing the mixed fractions, drying the eluted solutions (anhydrous $K_2CO_3$) and concentration a total of 24.37 g (60%) of product is obtained. This is then dried at 160° at 0.06 mm for 2 hours, $R_f$ 0.17 ($Al_2O_3$—10% methanol in ether). $\alpha_D = -6.1°$ (c=2, MeOH) TLC, $R_f$ 0.35, 2% MeOH in $CHCl_3$ on $Al_2O_3$ plates.

Analysis calc'd for $C_{33}H_{57}N_3O_6$: C, 66.97; H, 9.71; N, 7.10. Found: C, 66.65; H, 9.72; N, 7.20.

What is claimed is:

1. A process for preparing the optically active isomer [2R-[2α,3α,5(R*)]]-2,2'-[[5-[3-[(1,1-dimethylethyl)amino]-2-hydroxypropoxy]-1,2,3,4-tetrahydro-2,3-naphthalenediyl]bis(oxy)]-bis[N,N-dipropylacetamide] having the structure

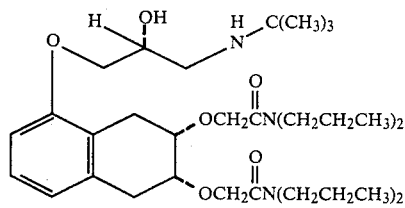

which comprises:

(1) reacting cis-5,6,7,8-tetrahydro-1,6,7-naphthalenetriol with an (R)-alkyl or aryl sulfonyl solketal, to form a mixture of d- and l-cyclic derivatives wherein the phenolic hydroxyl group is converted to an ether and the two alcoholic hydroxyl groups remain free, said cyclic derivatives having the structures

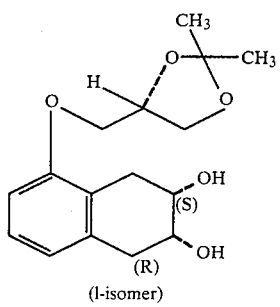
(l-isomer)

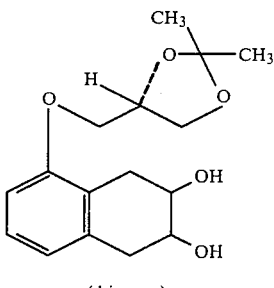
(d-isomer)

(2) separating out the l-cyclic derivative from said mixture;

(3) reacting said 1-cyclic derivative with N,N-dipropylchloroacetamide, N,N-dipropyliodoacetamide or, N,N-dipropylbromoacetamide, to yield a compound having the structure

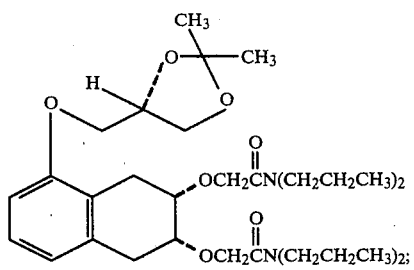

(4) hydrolyzing the acetonide ring of the compound produced in (3) to yield

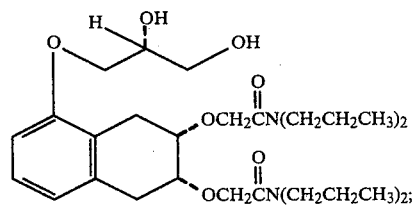

(5) reacting the compound produced in step (4) with mesitylenesulfonyl chloride to form

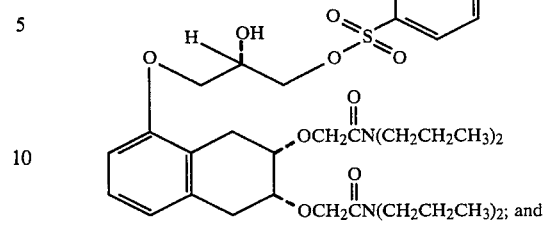

(6) removing the trimethylphenylsulfonyloxy group by reacting the compound produced in step (5) with t-butylamine to yield said optically active isomer.

2. The process as defined in claim 1 wherein said (R)-alkyl or arylsulfonyl solketal is (R)-2,2-dimethyl-1,3-dioxolane-4-methanol, 4-methylbenzenesulfonate ester ((R)-tosylsolketal).

3. The process as defined in claim 2 wherein said (R)-tosylsolketal is employed in a molar ratio to said naphthalenetriol of within the range of from about 1:1 to about 15:1.

4. The process as defined in claim 1 wherein said chloroacetamide is employed in a molar ratio to said 1-isomer of within the range of from about 2:1 to about 3:1.

5. The process as defined in claim 4 wherein said acetamide is N,N-dipropylchloroacetamide.

6. The process as defined in claim 1 wherein said mesitylene sulfonyl chloride is employed in a molar ratio to said compound produced in step (4) of claim 1 of within the range of from about 1:1 to about 1.5:1.

7. The process as defined in claim 1 wherein said t-butylamine is employed in a molar ratio to said compound produced in step (5) of claim 1 of within the range of from about 1:1 to about 20:1 or more.

* * * * *

UNITED STATES PATENT AND TRADEMARK OFFICE
CERTIFICATE OF CORRECTION

PATENT NO. : 4,326,076
DATED : April 20, 1982
INVENTOR(S) : Jerome L. Moniot et al.

It is certified that error appears in the above—identified patent and that said Letters Patent is hereby corrected as shown below:

On the title page, second line of the title, "2,2" should read --2,2'--.
Column 1, third line of the title, "2,2" should read --2,2'--.
Column 3, after line 21, insert --Isomer B--.
Column 6, line 17, "tetrahydrol" should read --tetrahydro-1--.

Signed and Sealed this

Seventeenth Day of August 1982

[SEAL]

Attest:

GERALD J. MOSSINGHOFF

Attesting Officer     Commissioner of Patents and Trademarks